United States Patent [19]
Noishiki et al.

[11] Patent Number: 4,806,595
[45] Date of Patent: Feb. 21, 1989

[54] METHOD OF PREPARING ANTITHROMBOGENIC MEDICAL MATERIALS

[75] Inventors: Yasuharu Noishiki, Tottori; Kazuhiko Kodaira, Mitaka; Masayasu Furuse, Sagamihara; Teruo Miyata, Tokyo, all of Japan

[73] Assignee: Koken Co., Ltd., Tokyo, Japan

[21] Appl. No.: 891,915

[22] Filed: Aug. 1, 1986

[30] Foreign Application Priority Data

Aug. 12, 1985 [JP] Japan ................................ 60-177450

[51] Int. Cl.$^4$ ............................ A61F 2/04; A61M 1/03
[52] U.S. Cl. ...................................... 525/54.2; 514/56; 514/822; 523/112; 623/1; 623/11; 623/12
[58] Field of Search ...................... 514/2, 801, 56, 822; 530/356; 424/95; 523/112; 128/DIG. 8, DIG. 22; 525/54.2; 623/66, 1, 2, 3, 11, 12

[56] References Cited

U.S. PATENT DOCUMENTS

| | | | |
|---|---|---|---|
| 4,001,200 | 1/1977 | Bonsen et al. | 530/305 |
| 4,690,973 | 9/1987 | Noishiki et al. | 427/2 |
| 4,704,131 | 11/1987 | Noishiki et al. | 427/2 |

FOREIGN PATENT DOCUMENTS

0092414 10/1983 European Pat. Off. .
58-180162 3/1983 Japan .
60-203264 6/1985 Japan .

OTHER PUBLICATIONS

Noishiki et al., "A Simple Method to Heparinize Biological Materials," *J. of Biomed. Mat. Res., vol. 20, 337-346 (1986)*.

*Primary Examiner*—John Kight
*Assistant Examiner*—Nathan M. Nutter
*Attorney, Agent, or Firm*—Armstrong, Nikaido, Marmelstein & Kubovcik

[57] ABSTRACT

In a method of preparing an antithrombogenic medical material having a heparinized collagen as an antithrombogenic component, there is provided a method comprising the steps of fixing a protamine to a collagen through a polyepoxy compound, and heparinizing the collagen by fixing heparin to the protamine.

16 Claims, No Drawings

METHOD OF PREPARING ANTITHROMBOGENIC MEDICAL MATERIALS

BACKGROUND OF THE INVENTION

1. Field of the Invention

The present invention relates to a method of preparing an antithrombogenic medical material 2. Description of the Prior Art Many medical materials used in the treatment of cardiovascular diseases are required to possess antithrombogenic properties. For instance, in the case of artificial blood-vessels, artificial valves, artificial hearts, and parts of artificial lung devices, if the surfaces coming into contact with blood possess blood coagulating properties, serious problems such as thrombosis may arise. In order to alleviate such problems, a variety of antithrombogenic medical materials consisting of synthetic polymer materials such as a polyurethane have been developed so far. These materials, however, do not always possess sufficient compatibility with endothelial cells and other cells of the living tissues, and therefore with these materials it was difficult to obtain satisfactory antithrombogenic properties.

Collagen is a protein, which is present in connective tissues and basement membranes of animal and is highly compatible with the cells Since collagen has no antithrombogenic property in itself, it is necessary to provide collagen with antithrombogenic properties in order to make the collagen usable as a medical material coming into contact with blood A simple and safe way of providing collagen with antithrombogenic properties is to combine heparin with the collagen through a protamine, in which the protamine is fixed to the collagen through a cross-linking agent For instance, Japanese Patent Application Laid Open No. 58-180162 discloses an antithrombogenic medical material consisting of a heparinized collagen in which heparin is attached to a protamine which is fixed to a collagen of animal origin through glutaraldehyde as a cross-linking agent.

The heparin in the heparinized collagen forms an ionic-bond with protamine and is released slowly in the living body to prevent blood from coagulating. It is further noted that since endothelial cells grow on the collagen base, antithrombogenic properties are maintained by the endothelial cells after the heparin is entirely released Since, however, glutaraldehyde is used as a cross-linking agent for fixing a protamine to the collagen, the resulting heparinized collagen will have a decreased flexibility and form constrictions or cracks when it is bent to a small radius of curvature. It is also likely that the glutaraldehyde discolors the heparinized collagen to brown, and that the glutaraldehyde is polymerized and released slowly as a polymer under some conditions in the living body, which may cause toxicity for a long period of time.

OBJECT AND SUMMARY OF THE INVENTION

It is therefore an object of the present invention to provide a method of preparing an antithrombogenic medical material that causes no toxicity and discoloration, and possesses a superior histocompatibility and superior antithrombogenic properties as well as superior physical characteristics, particularly, flexibility.

The above object is attained, according to the present invention, by a method of preparing an antithrombogenic medical material comprising a heparinized collagen as an antithrombogenic component, which comprises the steps of fixing a protamine to a collagen through a polyepoxy compound, and heparinizing the collagen by fixing heparin to the protamine.

DETAILED DESCRIPTION OF THE INVENTION

Collagens used in the present invention may be, for example, an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissues (ureter, blood-vessel, pericardium, etc).

Protamines used in the present invention, which are basic nucleoproteins, can be any one collected and purified from any animal, and may contain histones. However, protamines in the form of a salt-like combination with an inorganic salt or an organic salt are preferred, and, in particular, protamine sulfate or protamine hydrochloride is preferred.

Polyepoxy compounds used in the present invention may be, for example, glycol diglycidyl ether, polyol polyglycidyl ether, dicarboxylic acid diglycidylester and so on; in which a polyethylene glycol diglycidyl ether represented by the following formula (I):

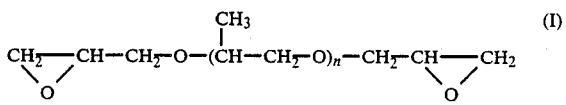

is particularly preferred because it can provide the heparinized collagen with both flexibility and hydrophilic properties.

Antithrombogenic medical materials prepared by the method according to the present invention may be composites of heparinized collagens and synthetic polymer materials. The synthetic polymer materials may be products prepared by weavng or knitting polyester fibers in the form of a tube, a plastic (for example, polycarbonate) molded article as in the circuit of an artificial lung device, and so on.

The heparinized collagens as an antithrombogenic component in the present invention may be prepared as follows.

In case of using an insoluble collagen as the collagen, the insoluble collagen is immersed in a 0.1% to 20% aqueous protamine and subsequently immersed in a 0.1% to 30%, preferably 1% to 10% aqueous solution of polyepoxy compound to fix the protamine to the collagen. The protamine-fixed collagen is then subjected to heparinization by immersing it in a 0.01% to 10%, preferably 0.1% to 2% aqueous heparin. In the above immersion treatments using each of the above-described aqueous solutions, the temperature may be in the range of from 5° C. to 90° C., preferably from 10° C. to 35° C., and the duration of immerison may be in the range of from 10 minutes to 24 hours, preferably from 30 minutes to 8 hours.

In an alternative embodiment in which a soluble collagen is used as the collagen, a heparinized collagen is obtained by the process in which a substrate such as a synthetic polymer material and the like is subjected to coating or impregnating treatment with a solution containing the soluble collagen and a protamine, and the substrate is subsequently immersed in an aqueous solution of a polyepoxy compound, and further immersed in a heparin aqueous solution.

In another embodiment, a heparinized collagen is obtained by the process in which a substrate such as a synthetic polymer material is subjected to a coating or impregnating treatment with a solution containing a soluble collagen, a protamine and a polyepoxy compound, and the substrate so treated is further immersed in an aqueous heparin.

In a further embodiment, a heparinized collagen is obtained by the process in which a substrate such as a synthetic polymer material is subjected to a coating or impregnating treatment with a solution containing a soluble collagen, a protamine, and heparin, and the substrate so treated is further immersed in an aqueous solution of a polyepoxy compound.

In a still further embodiment, a heparinized collagen is obtained by the process in which a substrate such as a synthetic polymer material is subjected to a coating or impregnating treatment with a solution containing a soluble collagen, a protamine, a polyepoxy compound and heparin and the substrate so treated is allowed to stand until the fixation of the protamine to the collagen through the polyepoxy compound is completed, and the substrate is subsequently dried In the foregoing processes, an insoluble collagen can be used in the form of a dispersion instead of the soluble collagen.

In the description of the foregoing heparinization, the solutions are implicitly aqueous solutions where the solvent consists only of water. It is to be noted, however, that aqueous solutions containing inorganic salts or organic substances, organic solvents or mixtures of these solvents can likewise be used.

A mucopolysaccharide such as hyaluronic acid, chondroitin sulfate, or dermatan sulfate can be added to any of the solutions in which collagen is present, which solutions are used in the coating or impregnating treatment of a substrate such as a synthetic polymer material, whereby the resulting heparinized collagen can be provided with an increased histocompatibility and hydrophilic properties.

According to the present invention, it is possible to obtain an antithrombogenic medical material comprising a heparinized collagen having both superior antithrombogenic properties and high flexibility.

The present invention will be understood more readily by reference to the following Examples; however, the Examples are intended to merely illustrate the present invention and are not to be construed whatsoever to limit the scope of the present invention.

In the following examples, polyethylene glycol diglycidyl ether used is Denacol EX-861 (Tradename of Nagase Sangyo K.K.) ($n \approx 22$ in the above formula (I)).

EXAMPLE 1

The carotid (inner diameter=3 mm; length=10 cm) of an adult dog was immersed in a 0.01% aqueous ficin (pH 7.4) at 25° C. for 24 hours to remove proteins other than collagen, and the carotid was then washed well with water. With one end of the carotid closed, the hollow portion of the carotid was filled with a 10% aqueous protamine sulfate (pH 5.0) and the carotid was allowed to stand at room temperature for one hour while air pressure of 100 mmHg was applied thereto After the excess of the solution was removed, the carotid was filled with a 10% aqueous polyethylene glycol diglycidyl ether (pH 8.0) and allowed to stand for one hour in the same xanner described above. Then the excess of the solution was removed. After the above treatments were repeated again, the carotid was washed well with water and was then immersed in a 1% aqueous heparin (pH 6.0) at room temperature for one hour. The carotid, after washed with water, was stored in a 70% aqueous ethanol to provide an artificial blood-vessel. No cracks and constrictions were observed in the artificial blood-vessel when it was bent by hand to a small radius of curvature.

ECAMPLE 2

A tube (inner diameter=3 mm; length=10 cm) for an artificial blood-vessel was prepared by knitting polyester fibers. One end of the tube was closed with a stopper, and the hollow of the tube was filled with a mixture of 10 ml of a 1% aqueous atelocollagen (pH 3), 5 ml of a 10% aqueous protamine sulfate (pH 5) and 3 ml of a 0.1% aqueous hyaluronic acid (pH 7). The tube was impregnated with the mixture by applying air pressure of 100 mmHg. After the excess of the solution was removed, a 0.1N aqueous sodium hydroxide with 10% polyethylene glycol diglycidyl ether concentration and 10% NaCl concentration was poured into the tube, and the tube was allowed to stand at room temperature for two hours. The tube was washed well with water and was immersed in a 1% aqueous heparin for one hour, followed by washing well with water. The tube was then immersed in a 5% aqueous glycerin for two hours and freeze-dried to provide an artificial blood-vessel. The resulting artificial blood-vessel was found to have the same satisfactory flexibility as obtained in Example 1.

Each of the artificial blood-vessels prepared in Exmaples 1 and 2 was implanted in the femoral aorta of an adult dog, and no thrombus was observed at all about three months threreafter, showing a 100% open rate.

EXAMPLE 3

In 90 g of water were dissolved 1 g of protamine sulfate, 0.1 g of heparin, and 10 g of a reagent-grade gelatin at 50° C. The resulting solution was coated on the inner surface of an artificial lung, and a 0.1N aqueous sodium hydroxide with 10% polyethylene glycol diglycidyl ether concentration and 10% NaCl concentration was poured into the artificial lung, which was then allowed to stand at 50° C. for two hours, washed well with water, and then air-dried.

In the resulting artificial lung applied to the box part connecting to the hollow fiber in the circuit of an artificial lung device, no thrombus iormation was observed at all for about 5 hours, showing superior antithrombogenic properties compared to those of conventional artificial lungs.

What is claimed is:

1. A method of preparing an antithrombogenic medical material comprising a heparinized collagen as an antithrombogenic component, which comprises the steps of fixing a protamine to a collagen through a polyepoxy compound, and heparinizing said collagen by fixing heparin to said protamine.

2. A method according to claim 1, wherein the protamine is at least one member selected from the group consisting of protamine sulfate and protamine hydrochloride.

3. A method according to claim 1, wherein the polyepoxy compound is at least one member selected from the group consisting of a glycol diglycidyl ether, a polyol polyglycidyl ether, and a dicarboxylic acid diglycidyl ester.

4. A method according to claim 3, wherein the polyepoxy compound is polyethylene glycol diglycidyl ether.

5. A method according to claim 1, wherein the antithrombogenic medical material is a composite of a heparinized collagen and a synthetic polymer.

6. A method according to claim 5, wherein the synthetic polymer material is one member selected from the group consisting of a product prepared by weaving or knitting polyester fibers in the form of a tube, and a plastic molded article.

7. A method according to claim 1, wherein a substrate is subjected to a coating or impregnating treatment with a solution which contains a collagen and a protamine, and said substrate is subsequently immersed in an aqueous solution of a polyepoxy compound, and then immersed in an aqueous heparin solution.

8. A method according to claim 1, wherein a substrate is subjected to a coating or impregnating treatment with a solution containing a collagen, a protamine and a polyepoxy compound, and said substrate is further immersed in an aqueous heparin solution.

9. A method according to claim 1, wherein a substrate is subjected to a coating or impregnating treatment with a solution containing a collagen, a protamine and heparin, and said substrate is further immersed in an aqueous solution of a polyepoxy compound.

10. A method according to claim 1, wherein a substrate is subjected to a coating or impregnating treatment with a solution containing a collagen, a protamine, a polyepoxy compound and heparin, and said substrate is allowed to stand until the fixation of said protamine to said collagen through said polyepoxy compound is completed, and said substrate is subsequently dried.

11. A method according to claim 7, wherein at least one mucopolysaccharide selected from the group consisting of hyaluronic acid, chondroitin sulfate and dermatan sulfate is added to said solution which contains a collagen and a protamine.

12. A method according to claim 8, wherein at least one mucopolysaccharide selected from the group consisting of hyaluronic acid, chondroitin sulfate and dermatan sulfate is added to said solution which contains a collagen, a protamine and a polyepoxy compound.

13. A method according to claim 9, wherein at least one mucopolysaccharide selected from the group consisting of hyaluronic acid, chondroitin sulfate and ermatan sulfate is added to said solution which contains a collagen, a protamine and heparin.

14. A method according to claim 7 or 9, wherein at least one mucopolysaccharide selected from the group consisting of hyaluronic acid, chondroitin sulfate and dermatan sulfate is added to said solution which contains a polyepoxy compound.

15. A method according to claim 7 or 8, wherein at least one mucopolysaccharide selected from the group consisting of hyaluronic acid, chondroitin sulfate and dermatan sulfate is added to said solution which contains heparin.

16. A method according to claim 10, wherein at least one mucopolysaccharide selected from the group consisting of hyaluronic acid, chondroitin sulfate and dermatan sulfate is added to said solution which contains a collagen, a protamine, a polyepoxy compound and heparin.

* * * * *